(12) United States Patent
Schüttler et al.

(10) Patent No.: US 10,898,092 B2
(45) Date of Patent: Jan. 26, 2021

(54) IMPLANTABLE CUFF ELECTRODE

(71) Applicant: CorTec GmbH, Freiburg (DE)

(72) Inventors: Martin Schüttler, Freiburg (DE); Juan Sebastian Ordonez, Freiburg (DE); Jörn Rickert, Freiburg (DE); Thomas Stieglitz, Freiburg (DE)

(73) Assignee: CorTec GmbH, Freiburg (DE)

( * ) Notice: Subject to any disclaimer, the term of this patent is extended or adjusted under 35 U.S.C. 154(b) by 88 days.

(21) Appl. No.: 16/113,430

(22) Filed: Aug. 27, 2018

(65) Prior Publication Data
US 2019/0060641 A1 Feb. 28, 2019

Related U.S. Application Data

(63) Continuation of application No. PCT/EP2017/054259, filed on Feb. 23, 2017.

(30) Foreign Application Priority Data

Feb. 29, 2016 (DE) .................. 10 2016 103 597

(51) Int. Cl.
*A61B 5/04* (2006.01)
*A61N 1/05* (2006.01)
*A61N 1/36* (2006.01)

(52) U.S. Cl.
CPC ........ *A61B 5/04001* (2013.01); *A61N 1/0556* (2013.01); *A61N 1/3605* (2013.01)

(58) Field of Classification Search
CPC .......................... A61B 5/04001; A61N 1/0556
See application file for complete search history.

(56) References Cited

U.S. PATENT DOCUMENTS

| | | | | |
|---|---|---|---|---|
| 4,602,624 A * | 7/1986 | Naples | ................ | A61N 1/0556 607/118 |
| 5,487,756 A * | 1/1996 | Kallesoe | .............. | A61N 1/0556 600/381 |
| 5,938,596 A * | 8/1999 | Woloszko | ............ | A61N 1/0556 600/377 |
| 8,417,343 B2 * | 4/2013 | Bolea | .................. | A61N 1/3606 607/42 |
| 8,612,025 B2 * | 12/2013 | Neisz | .................. | A61N 1/0556 607/118 |
| 8,965,499 B2 * | 2/2015 | Cowley | ................ | A61N 1/0556 607/2 |
| 9,227,053 B2 * | 1/2016 | Bonde | ................. | A61N 1/0556 |
| 9,283,379 B2 * | 3/2016 | True | .................... | A61N 1/0556 |

(Continued)

OTHER PUBLICATIONS

International Search Report issued for International Patent Application No. PCT/EP2017/054259 dated Jul. 24, 2017.

*Primary Examiner* — Lee S Cohen
(74) *Attorney, Agent, or Firm* — Myers Wolin, LLC

(57) ABSTRACT

An implantable cuff electrode having a flexible cuff in form of a tube having a longitudinal slot, wherein the longitudinal slot defines a first edge and a second edge on the cuff, wherein a first lip is arranged at the first edge of the longitudinal slot, and a second lip is arranged at the second edge of the longitudinal slot, and wherein the longitudinal slot can be sealed by the first lip and the second lip in that the first lip and the second lip extend at least partially on the cuff jacket of the cuff one lying on top of the other, and the second lip holds the first lip in position by means of a surface pressure onto the cuff jacket.

9 Claims, 5 Drawing Sheets

(56) References Cited

U.S. PATENT DOCUMENTS

2006/0116739 A1* 6/2006 Betser ............... A61N 1/0556
607/48
2010/0298916 A1 11/2010 Rabischong et al.
2013/0261721 A1 10/2013 Ben-David et al.

* cited by examiner

IMPLANTABLE CUFF ELECTRODE

CROSS-REFERENCE TO RELATED APPLICATIONS

This application is a continuation application under 35 U.S.C. § 120 of International Application PCT/EP2017/054259, filed Feb. 23, 2017, which claims priority to German Patent Application 10 2016 103 597.1, filed Feb. 29, 2016, the contents of each of which are incorporated by reference herein.

FIELD

The present invention relates to a cuff electrode implantable into the human or animal body and a method for its production.

BACKGROUND

In the field of medical engineering, implantable systems are used so as to interact with the neural system, and to bridge or restore lost body functions, as well as to remedy dysfunctions of organs. For this, cuff electrodes are required and are positioned around the nerves. On the inner side, the cuffs are provided with electrical contacts, which allow for recording electrical activity and/or for electrically influencing the natural nerve activity. Requirements to a cuff electrode are, amongst others:

The electrical contacts should be located in the immediate vicinity of the target nerve in order to allow for a good electrical coupling to the nerve tissue.

The cuff has to ensure a very good electrical insulation against the surroundings over its entire length in order to prevent that during the recording of nerve signals, electrical signals, for example, from adjacent muscle tissue, coupled into the record.

The cuff should be made of a soft material so as to substantially avoid unnecessary mechanical irritation and/or impairment of the nerves, for example, due to hard or even sharp edges.

The cuff should allow for the nerve swelling temporarily, for example, as a reaction to the implantation procedure; namely, if a nerve swells within a cuff having a non-modifiable diameter, the blood vessels within the nerve may be pinched off, and the nutrition supply of the nerve is interrupted resulting in the effect of nerve damage.

In particular, with respect to cuff electrodes, which are intended for enclosing nerves having small diameters of some 10 µm up to a few 100 µm, the requirements mentioned above in combination are not satisfactorily met by existing technologies (materials and designs), amongst others, because soft cuffs typically are hand-made (and therefore, the required accuracy for this geometrical dimension is not sufficient) or by means of photolithographic methods, in which typically much harder materials (e.g., polyimide) are used as cuff material.

So-called spiral cuffs are known, which typically require more than one winding in order to seal tightly against the body tissue. Because the important electrical structures are located on the inner jacket of the spiral cuff, the spiral cuff, prior to being placed around the nerve, has to be rolled up completely for one time, which in turn subjects the delicate embedded metal structures to mechanical stress. If the desired diameters of the cuff are very small, for example, smaller than 1 mm, larger rolling forces for opening the cuff are required. This conflicts with the requirements of the mechanical properties of the cuff, which has to enclose a smaller and thus softer nerve: larger rolling forces require a thicker material, which in turn, increases the flexural rigidity. If the embedded metal is deformed plastically only during rolling up of the cuff, the returning of the cuff to the target diameter is not readily possible.

SUMMARY

It is an object of the present invention to provide a cuff electrode, which is suitable for thinner nerves (e.g., smaller than 1 mm), as well as to provide a production method for this.

Accordingly, an implantable cuff electrode is provided, comprising:

a flexible cuff having the shape of a tube with a longitudinal slot, wherein the longitudinal slot defines a first edge and a second edge on the cuff, wherein a first lip is arranged at the first edge of the longitudinal slot, and a second lip is arranged at the second edge of the longitudinal slot, and wherein the longitudinal slot can be sealed by the first lip and the second lip in that the first lip and the second lip extend one on top of the other at least partially on the cuff jacket of the cuff, and the second lip retains the first lip in position on the cuff jacket by surface pressure.

Preferred embodiments are as follows:

The second lip may be movable in circumferential direction of the cuff relative to the first lip and the cuff jacket, while maintaining the sealing of the longitudinal slot.

The second lip may be movable upon modifying the width of the longitudinal slot, while maintaining the sealing of the longitudinal slot.

The cuff may be opened at the longitudinal slot by means of moving the second lip against the pressure and/or of the cuff jacket in circumferential direction under elastic deformation of the second lip.

Upon modification of the distance of the edges with respect to each other in circumferential direction of the cuff, the lips may be movable relative to the cuff while maintaining the sealing of the longitudinal slot.

The inner diameter of the cuff may vary in longitudinal direction, in particular, towards the ends.

An electrode array may be provided on the inner wall of the cuff.

The electrode array may comprise at least two sensor surfaces separated from each other, which are arranged along a line in longitudinal direction of the cuff, wherein the at least two sensor surfaces are connected to each other electrically via at least one conductor portion, wherein the at least one conductor portion is deformable elastically during opening and closing of the cuff.

The at least one conductor portion may be arranged on the inner wall, and may comprise meandering patterns arranged at the inner wall.

The line may be located diametrically opposed to the longitudinal slot in cross section, and may comprise the vertex of the bending line of the carrier in cross section.

The sensor surfaces may be coupled to electrical conductors, which are guided outwards from the cuff.

The cuff may be a silicone tube, in which the electrode array is arranged, wherein the electrode array is embedded in a carrier made from silicone material, and wherein the carrier has two longitudinal sides, which are guided out of the silicone tube and which form the lips.

A cover layer may be formed above the longitudinal slot, which contributes to the fixation of the lips and/or to the sealing of the longitudinal slot.

The cover layer may comprise silicone material.

The first lip may project beyond the second lip and beyond the cover layer.

The carrier may have lower thicknesses at the longitudinal sides than in that area, which is arranged inside the silicone tube.

The carrier may have a rigidity decreasing from its longitudinal center axis towards its longitudinal sides.

The invention also comprises a method for producing an implantable cuff electrode, in particular, according to any one of the preceding claims, comprising:
- applying a first layer made from silicone rubber diluted with n-heptane on an auxiliary carrier,
- curing the first layer,
- cutting openings into the first layer,
- laminating a metal foil onto the first layer,
- reducing the thickness of the metal foil at spots, which are intended as contact electrodes,
- structuring the metal foil,
- applying a second layer made from silicone rubber diluted with n-heptane,
- connecting the first layer from silicone rubber and the second layer from silicone rubber by vulcanization,
- exposing the spots, which are intended as contact electrodes,
- reducing the thickness of the layer made from silicone rubber at two opposing edges,
- removing the auxiliary carrier,
- applying wires at the backside of the array,
- applying a third layer made from silicone rubber diluted with n-heptane onto the backside of the array,
- bending the array over the two edges, and introducing the bent array into the silicone tube with the longitudinal slot such that the two edges are located outside of the silicone tube,
- curing the third silicone layer,
- arranging the rims and fixing the rims with a silicone rubber layer, and
- curing the fourth silicone rubber layer.

The metal layer may be roughened at the spots, which form the electrodes.

The metal may be structured by means of laser beams.

The metal foil may be structured in a meandering manner in transverse direction.

Silicone is an elastic material of particular softness with excellent mechanical and dielectrical longtime stability in a biological environment, and of excellent biological compatibility. Silicone and electrode contacts are deformed into a tube-shaped cuff such that the result meets the requirements mentioned above. It should be emphasized that with respect to the cuff electrode technology presented here, the closing mechanism, in contrast to the prior art, provides an electrical sealing mechanism of the cuff at the external side of the cuff. Such a construction may be produced by combination of a few precision mechanical steps and high precision laser micro-structuring.

The (self-sealing) closure mechanism is arranged at the outer side of the cuff, and does not require a sealing lip protruding into the internal space of the cuff.

The closing mechanism is formed such that both sealing lips can be gripped easily by respectively one tweezer. By pulling the tweezer apart, the cuff is opened.

The electrical contacts within the cuff are configured such that an elastic opening of the cuff is enabled without the metal contacts being deformed plastically.

The wall of the cuff may become thinner gradually in longitudinal direction towards the ends, and thereby, the rigidity may decrease. Thereby, the risk of a mechanical irritation of the nerve at the ends of the cuff is reduced.

For the user, the following advantages are provided.

By maximizing the usable surface on the inner wall of the cuff, a better electrical coupling (larger contact areas or a higher number of small contact areas) can be achieved. This is possible due to relocating the closing mechanism to the outer wall of the cuff.

Even with nerve swellings, the nerve is not compressed by the cuff, because silicone lips, which form the closing mechanism at the outer wall, glide along each other for increasing the diameter of the cuff without impairing the closing quality (electrical insulation).

Facilitated handling of the cuff electrodes by optical marking the outer edge of the silicone lips. Here, the lips may be simply gripped respectively by means of a tweezer or a clamp and may be opened in order to be able to place the nerve into the opened cuff.

High reliability of the metal contacts due to the option of subdividing the contacts into several contact islands connected to each other electrically such that upon opening of the cuff, no metal is deformed plastically (counteracting the reverse forming during closing), but to rather a hinge-like unfolding of the cuff is enabled.

By gradually thinning the cuff body at the ends, the rigidity is reduced, and the risk of a mechanical irritation of the nerve, in particular, at the edges of the cuff, is minimized.

BRIEF DESCRIPTION OF THE DRAWINGS

The invention and embodiments are described in further detail by means of the drawing, in which.

DETAILED DESCRIPTION

Figure 1:
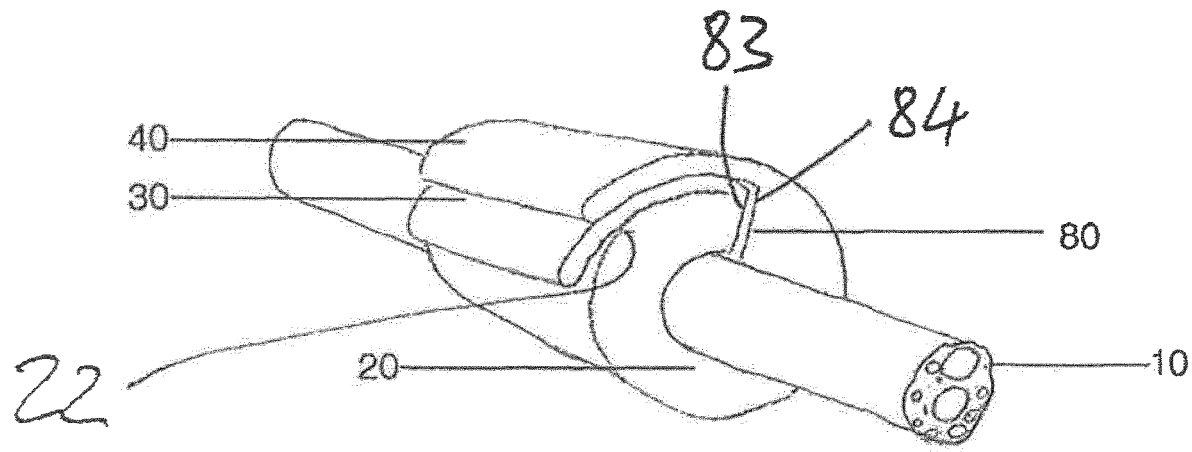
FIG. 1 is a perspective view of the cuff electrode in longitudinal direction in a sealing state.

FIG. 1 shows a perspective view of the implantable cuff electrode in longitudinal direction in a sealing state. Cuff 20 comprises the first lip 30 and the second clip 40. The cuff electrode is wound around the nerve 10. The cuff electrode can be arranged around the nerve 10, i.e., can be positioned around the nerve 10 like a jacket in longitudinal direction of the nerve. The cuff electrode thus encloses the nerve with its cuff 20.

In the entire description, the expression "in longitudinal direction" (of the cuff) means "axially". Cross-sections are oriented perpendicular to this.

Figure 2:
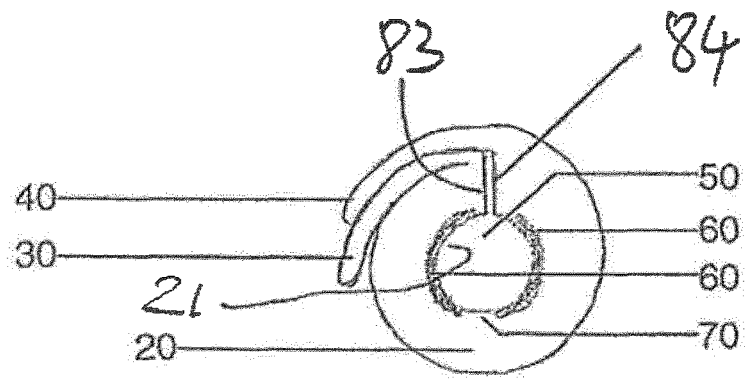
FIG. 2 is a cross-sectional view of the cuff electrode in a sealing state.

FIG. 2 shows a cross-sectional view through the cuff electrode in a sealing state. The sensor surface 60 is configured such that it is interrupted at at least one spot 70. The lips 30 and 40 both are located outside of the cuff 20 and thereby allow for an optimum use of the inner wall 21 of the cuff for the electrode contacts 60.

Figure 3:
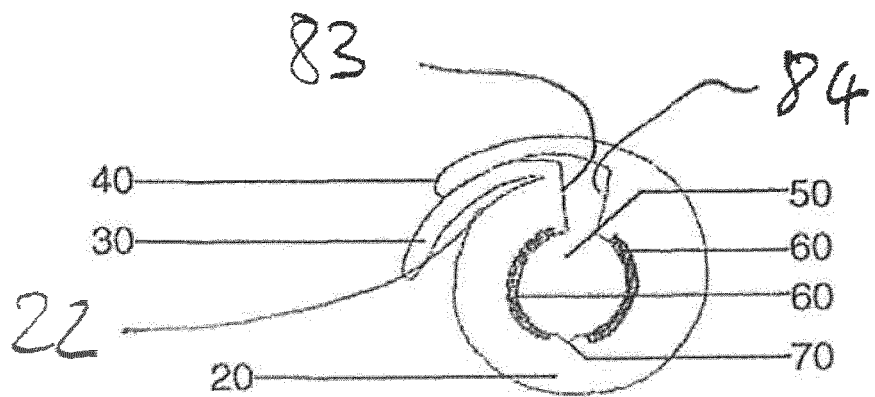
FIG. 3 is a cross-sectional view so the cuff electrode in a sealing state, however, with a swelling nerve (the longitudinal slot is slightly enlarged)

FIG. 3 shows a cross-sectional view through the cuff electrode in a sealing state, however, with a swelling nerve (the longitudinal slot is slightly enlarged).

Figure 4:
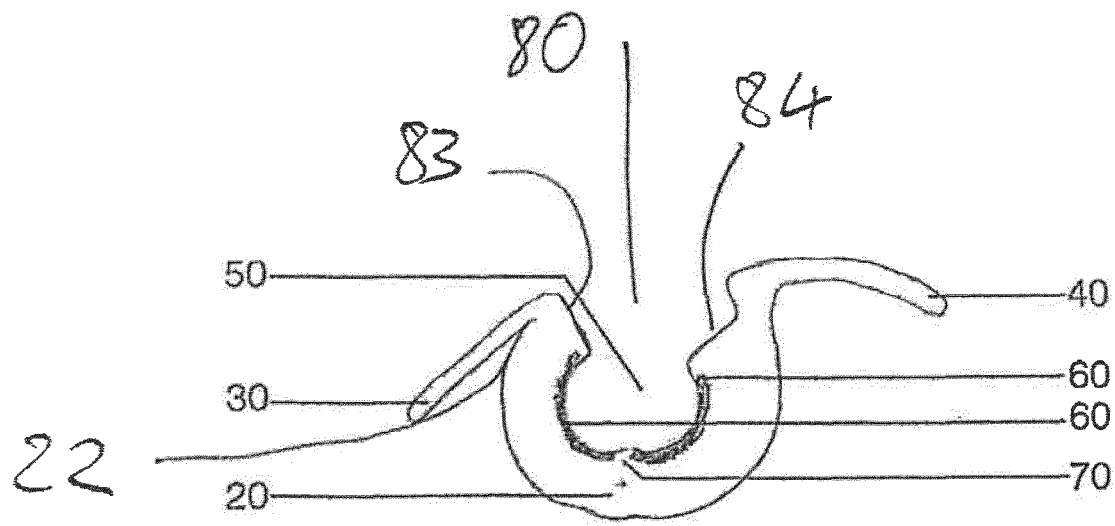
FIG. 4 is a cross-sectional view through the cuff electrode in an opened state.

FIG. 4 shows a cross-sectional view through the cuff electrode in an opened state.

The implantable cuff electrode of the invention thus comprises a flexible cuff 20 in form of a tube having a longitudinal slot 80, wherein the longitudinal slot 80 defines a first edge 83 and a second edge 84 of the cuff 20, wherein a first lip 30 is arranged at the first edge 83 of the longitudinal slot 80, and a second lip 40 is arranged at the second edge 84 of the longitudinal slot 80, and wherein the longitudinal slot 80 can be sealed by the first lip 30 and the second lip 40 in that the first lip 30 and the second lip 40 extend at least partially on the cuff jacket 22 of the cuff one lying on top of the other, and the second lip 40 retains the first lip 30 in position by applying surface pressure onto the cuff jacket 22.

At least the second lip 40 is movable in circumferential direction of the cuff 20 relative to the first lip 30 and to the cuff jacket, while maintaining the sealing of the longitudinal slot 80.

The second lip 40 is movable additionally upon modification of the width of the longitudinal slot 80, while maintaining the sealing of the longitudinal slot.

As is shown in FIG. 3, the lips 30, 40 are movable upon modification of the distance of the edges with respect to each other in circumferential direction of the cuff 20 relative to the cuff 20, while maintaining the sealing of the longitudinal slot.

As is shown in FIG. 4, the cuff 20 may be opened at the longitudinal slot by moving the second lip 40 under elastic deformation of the second lip 40 against the pressure and/or the cuff jacket in circumferential direction.

The inner diameter of the cuff 20 may vary in longitudinal direction, for example, it may increase towards the ends.

An electrode array 60 is arranged on the inner wall 21 of the cuff, as is shown in FIG. 3 and FIG. 4.

Figure 5:
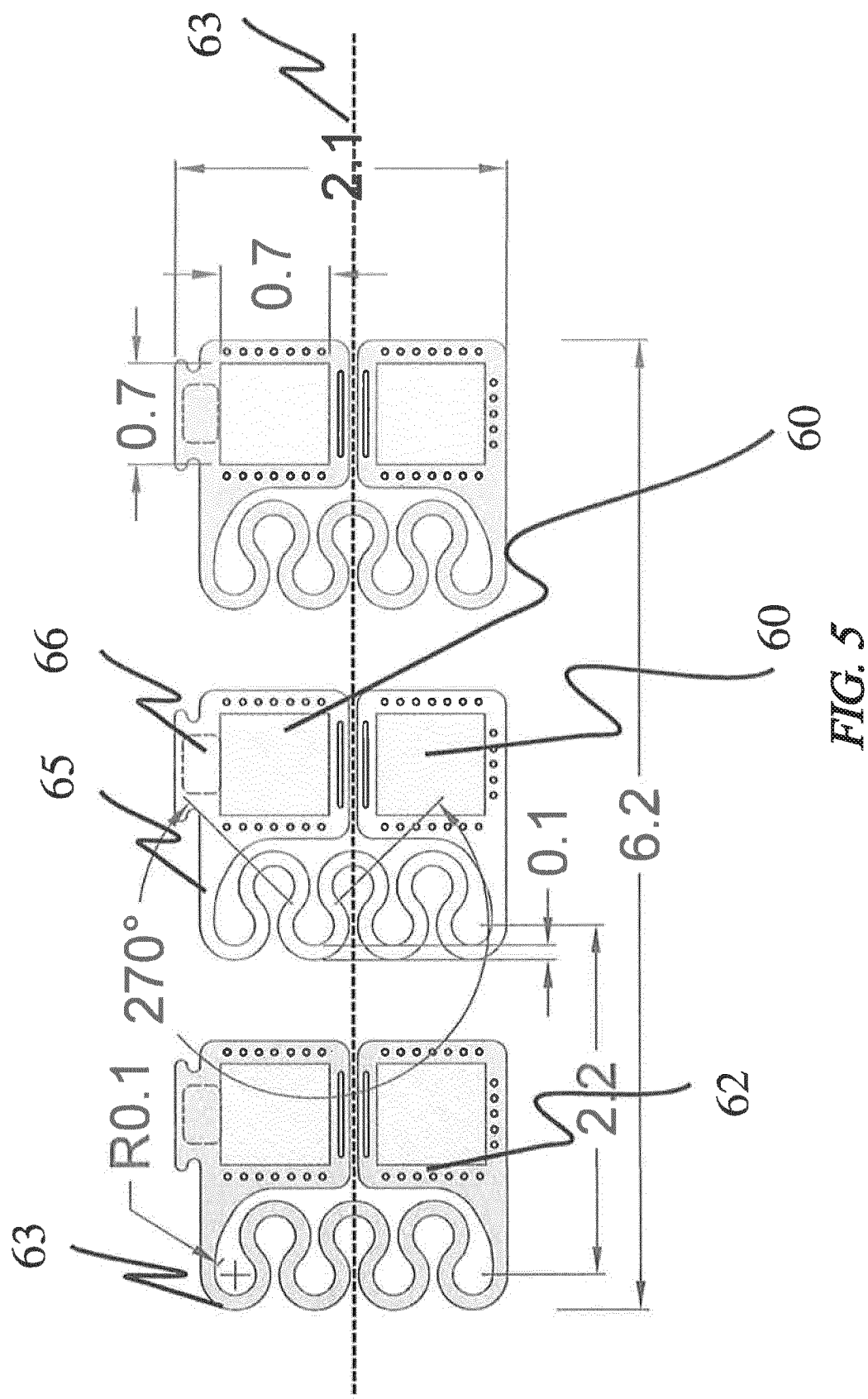
FIG. 5 is an electrode array in an "unwound" view.

FIG. 5 shows an electrode array 60, 65 with exemplary dimensions. The electrode array 60, 65 comprises at least two sensor surfaces 60 separated from each other, which are arranged alongside aligned 70 in longitudinal direction of the cuff 20, wherein the at least two sensor surfaces 60 are in electrical connection with each other via at least one conductor portion 65, wherein the at least one conductor portion 65 during opening and closing of the cuff 20 is deformable elastically.

The at least one conductor portion 65 is arranged in the inner wall 21 and comprises meandering patterns 63 arranged in the inner wall 21.

In cross section of the cuff electrode, the line 70 opposes the longitudinal slot 80 diametrically, and comprises the vertex of the bending line in cross section of the carrier 25, cf. FIGS. 2 to 4.

The sensor surfaces 60 are coupled to electrical conductors (not shown), which are guided to the outside from the cuff 20. For this, the electrode array 60, 65 comprises contact pads 66, which the connectors are connected to.

In particular, the cuff 20 may be a silicone tube, in which the electrode array 60, 65 is arranged, wherein the electrode array 60, 65 itself is embedded into a carrier 25 also made from silicone material, and wherein the carrier 25 has two longitudinal sides, which are guided out of the silicone tube and form the first lip 30 and the second lip 40.

A cover layer 45 may be arranged above the longitudinal slot 80, which contributes to the fixation of the lips 30, 40 and/or to the sealing of the longitudinal slot 80. The cover layer 45 may also comprise silicone material. The first lip 30 may project beyond the second lip 40 and beyond the cover layer 45.

The carrier 25 may have lower thicknesses at the longitudinal sides than in that area, which is located in the interior of the silicone tube. The carrier 25 may have a rigidity decreasing from its longitudinal center axis towards its longitudinal sides.

The production method according to the invention allows the shaping of the cuff electrode by a pre-shaped half-cylindrical mold having a desired diameter and with desired mechanical properties of the cuff electrode.

By the process sequence, the inner diameter of the 3-D structure may be defined with modified thickness of the carrier silicone (laser electrode array). A local structuring of the carrier silicone allows a local thickness adjustment of the carrier structure so as to maintain the lip closing mechanism independently of the diameter.

The cuff comprises a self-closing mechanism, which returns the cuff back to its target diameter independently of the opening load and closes the longitudinal slot sealingly.

By the position and architecture of the embedded metal, the metal does not exert any force to the cuff, and thus does not impair the target shape of the cuff.

The closing lips have a closing force independent of the cuff diameter, which ensures a tight sealing of the cuff, even with possible swellings of the nerves. At the same time, these closing lips serve as gripping structures, which enable the opening of the cuff without exerting any force on the critical metal structures.

A gradual modification of the cuff rigidity towards the edge enables the protection of the nerves and prevents the sharp bending of the nerves at an edge at the ends of the cuff.

The targeted laser structuring allows a local modification of the mechanical properties of the metal-bearing silicone structure. Thus, the own force of the shaped carrier foil can be adapted locally, and a reformation of the planar structure is enabled.

The targeted laser structuring allows for a local modification of the geometrical properties of the metal-bearing silicone structure. Thus, the inner diameter of the cuff 20 can be modified by means of the carrier foil locally without changing the properties of the closing mechanism.

The gradual adjustment of the cuff rigidity towards the edge allows for the protection of the nerves and prevents the sharp bending of the nerves at the edges at the ends of the cuff.

The production method is based on a planar electrode array, which is based on the structuring of metal foil by means of laser beams and silicone rubber. The electrode array is introduced into a silicone tube for subsequent 3-D shaping. The electrode array is produced from silicone rubber for medical applications (Medical Grade PDMS, MED 1000) and platinum foil having a starting thickness of 12.5 µm (99.5% Pt). Instead of the Pt foil, also foil from PtIr may be used (e.g. 90% Pt, 10% Ir). For structuring the electrode array, a Nd:YVO$_4$ picoseconds laser with a third harmonic wave of 355 nm may be used.

As auxiliary carrier during the production process, a 2 inch by 2 inch aluminum substrate is used, which is provided with a self-adhesive film, which is detached at the end of the structuring process.

The PDMS is diluted in a ratio of 1:1 with n-heptane in order to reduce its viscosity and to enable its application (spin coating).

Figure 6A:
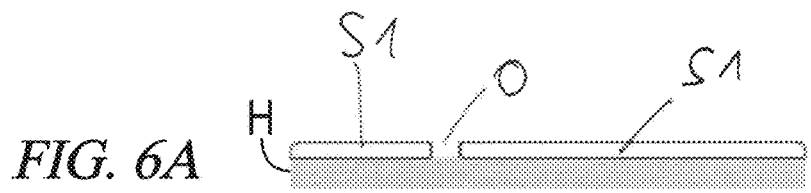
FIGS. 6A-6L shows the production process.
Figure 6B:
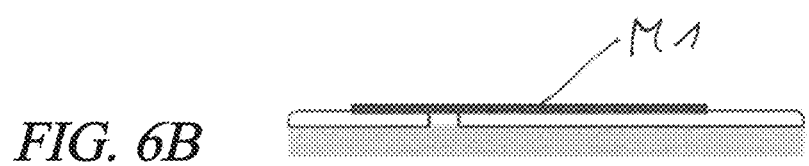
Figure 6C:
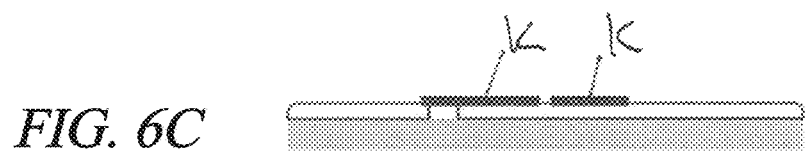
Figure 6D:
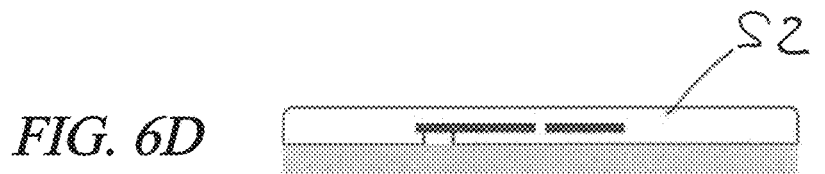
Figure 6E:
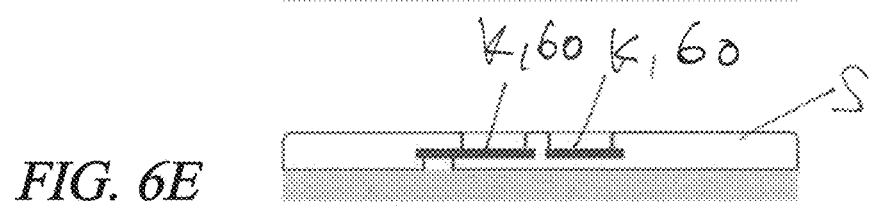
Figure 6F:
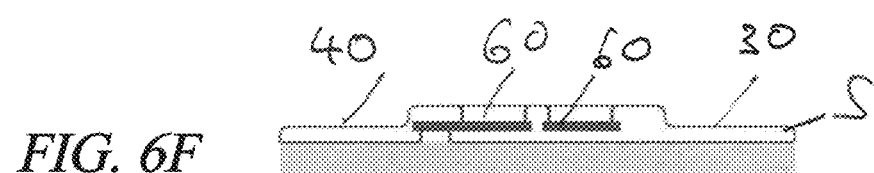
Figure 6G:
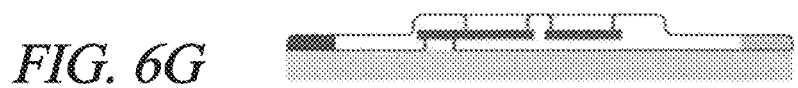
Figure 6H:
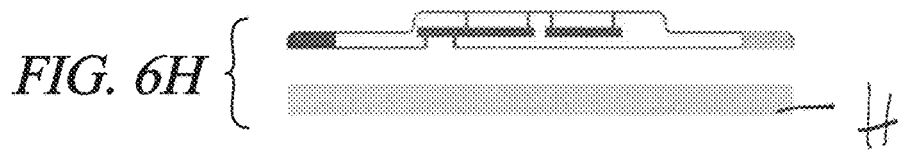
Figure 6I:
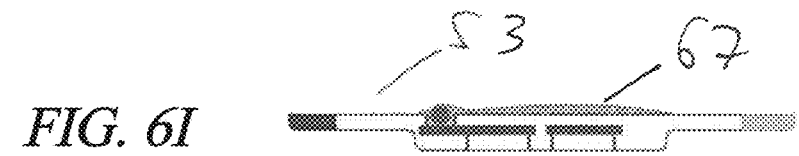

The method for producing an implantable cuff electrode comprises the following steps:

a) application of a first layer made from silicone rubber diluted with n-heptane (PDMS) onto an auxiliary carrier H, preferably, this layer is 100 µm thick and, preferably, is spin coated onto the auxiliary carrier provided with the self-adhesive film;

b) curing the first layer S1;

c) cutting openings O into the first layer S1, these openings form the openings in the connection pads, at which the wires are connected (FIG. 6A);

d) laminating a metal foil M1 onto the first layer; the metal foil, preferably, is a cleaned Pt foil (FIG. 6B);

f) reducing the thickness of the metal foil at the spots K, which are intended as contact electrodes 60;

f) structuring the metal foil (FIG. 6C); the excessive material is removed from the surface;

g) application of a second layer S2 made from silicone rubber diluted with n-heptane, in order to embed the metal foil, preferably, diluted PDMS of a thickness of 100 µm (FIG. 6D); the inner diameter of the cuff electrode may be modified by varying the thickness of this layer;

h) connecting the first layer Si made from silicone rubber and the second layer S2 made from silicone rubber to a silicone rubber layer S by means of vulcanization, i) exposing the spots, which are intended as contact electrodes 60, preferably, by means of the laser (FIG. 6E); by means of the laser, also the planar spots of the contact electrodes may be roughened such that a higher charge induction capability is created;

j) reducing the thickness of the silicone rubber layer at two opposing longitudinal edges (FIG. 6F); preferably down to 75 µm; the areas of reduced thickness are guided from the cuff interior to the outside and form the lips 30, 40 of the cuff electrode; by reducing of the thickness of the silicone rubber layer, a better shapability is achieved during the last formation step (FIG. 6K); in this step, the outer shape of the silicone rubber layer may be cut;

l) after drying, the two lips 30, 40 are dyed, preferably, by means of colors being optically distinguishable; this allows for a better distinguishability of the lips during implantation of the cuff electrode (FIG. 6G);

m) removal of the auxiliary carrier H (FIG. 6H);

n) attaching wires 67 at the backside of the array, preferably, by means of soldering of wires having a diameter of 70 to 80 µm;

o) applying a third layer S3 made from silicone rubber diluted with n-heptane on the backside of the array (FIG. 6I).

Figure 6J:
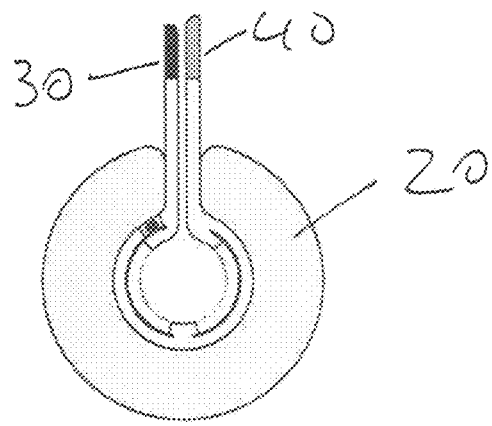
Figure 6K:
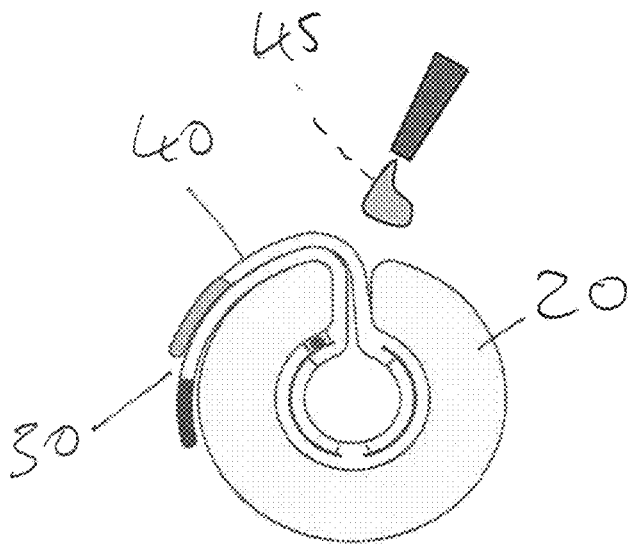
Figure 6L:
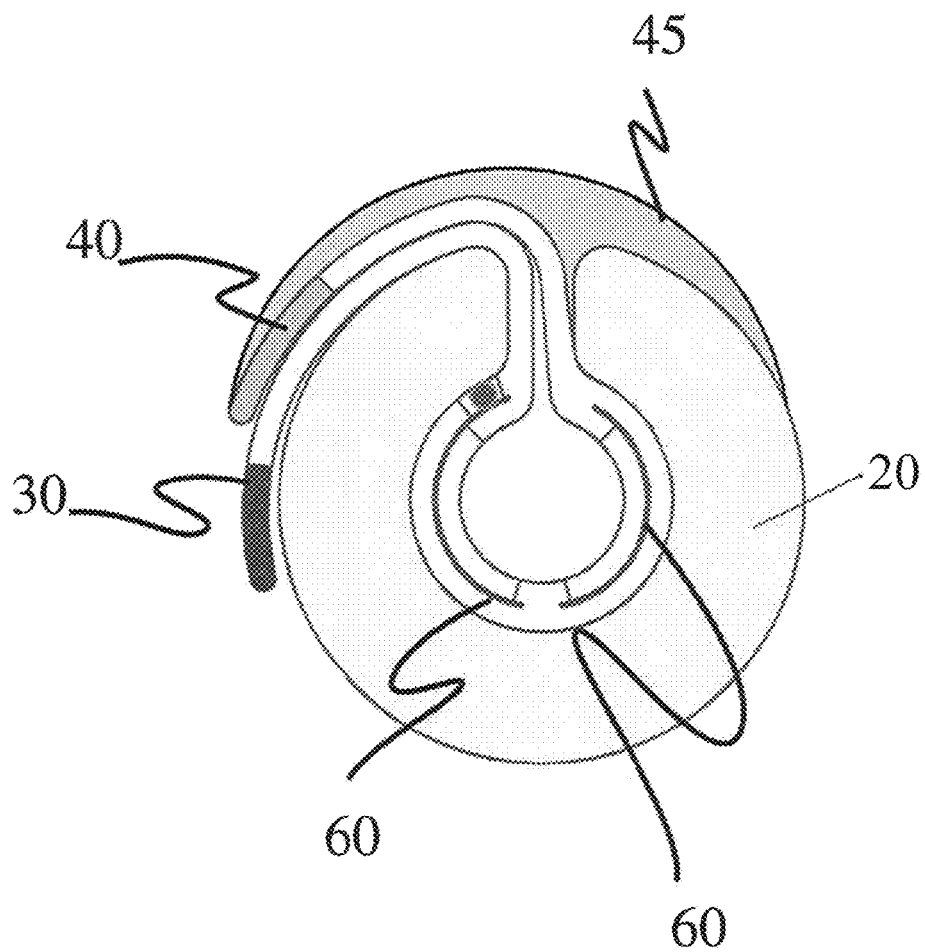

Now, the electrode array is ready to be introduced into the silicone tube. With respect to the silicone tube, preferably, an USP class VI silicone tube is concerned having an inner diameter matching the outer diameter of the nerve and a wall thickness of 300 to 500 µm. The silicone tube is also cut to the desired length, and is provided with a straight longitudinal slot 80 in parallel to the longitudinal axis of the silicone tube.

p) bending the array over the two edges such that the two lips 30, 40 contact each other. The cross-sectional bending line of the array without the lips 30, 40 describes a circular line; introducing the bent array into the silicone tube with the longitudinal slot such that the two lips pass through the longitudinal slot 80 and are located outside of the silicone tube (FIG. 6J). The introduction of the electrode array 60, 65 into the silicone tube may also be carried out by means of a cannula.

q) Curing the third silicone rubber layer; hereby, the cuff electrode may be stabilized in a half-pipe Teflon® mold (diameter corresponds to the outer diameter of the silicone tube).

r) Folding the lips 30, 40 onto the jacket of the silicone tube and fixing the outer lip 40 with a reinforcement layer 45 made from diluted silicone rubber in order to retain the lip 40 in its position. The reinforcement layer together with the two lips forms a self-closing system (FIG. 6K).

s) Curing the reinforcement layer. The cuff electrode according to FIG. 6L is created.

The two lips 30, 40 provide a closing mechanism, which does not contribute to the compression of the nerve 10. The upper second lip 40 is newly formed as it is treated with the n-heptane diluted PDMS after the bending, whereas the lower lip, namely that one which directly contacts the silicone tube, is only held in position by the upper lip. The lower lip, thus, acts against the upper lip, and thus, creates a good contact between the lips in the longitudinal slot. Moreover, this creates the self-closing closing mechanism.

Preferably, the lips are free of metal in order to improve the sealing effect at the slot after the implantation.

During bending of the cuff electrode so as to be opened prior to the implantation around the nerve, the cuff electrode is subject to high pressure or tensile loads over its cross-section.

Due to the substantially lower extensibility of metal compared to silicone rubber, a detachment (delamination) of the silicone rubber from the metal may occur.

On the other hand, breakages may occur there, where the metal is subject to the highest load during bending. This is the vertex line of the bent metal, which extends along the symmetry line of the carrier in longitudinal direction.

In order to avoid breakage, the metal is interrupted along the vertex line (symmetry line). The electrode surface, there, thus is divided into parts. In order to create an electrical connection of both electrode surfaces, the two electrode surfaces are connected to each other via a metal path. This metal path extends in a meandering manner in circumferential direction of the bent electrode array, namely, transversely with respect to the symmetry line of the carrier. Preferably, there are more than one meandering portions and the meandering portions preferably describe three-quarter circles. The metal path, preferably, has a width of 100 µm, and the meandering portions extend in three-quarter loops. The loops, preferably, have a diameter of 0.1 mm.

In longitudinal direction, there may be formed several electrodes, e.g., two or three electrodes.

A typical length of the cuff electrode is 6.2 mm, the outer diameter may be 2.1 mm.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwith-

The invention claimed is:

1. An implantable cuff electrode, comprising:
a flexible cuff having the shape of a tube with a longitudinal slot, wherein the longitudinal slot defines a first edge and a second edge on the cuff, wherein a first lip is arranged at the first edge of the longitudinal slot and a second lip is arranged at the second edge of the longitudinal slot, wherein the longitudinal slot can be sealed by the first lip and the second lip in that the first lip and the second lip extend at least partially on a cuff jacket of the cuff one on top of the other, and the second lip holds the first lip in position by applying a surface pressure onto the cuff jacket, wherein at least the second lip is movable in a circumferential direction of the cuff relative to the first lip and to the cuff jacket, while maintaining the sealing of the longitudinal slot, and wherein an electrode array is arranged on an inner wall of the cuff.

2. The implantable cuff electrode according to claim 1, wherein at least the second lip is movable upon modification of the width of the longitudinal slot, while maintaining the sealing of the longitudinal slot.

3. The implantable cuff electrode according to claim 1, wherein the cuff can be opened at the longitudinal slot by moving the second lip (40) under elastic deformation of the second lip against the pressure and/or the cuff jacket in circumferential direction.

4. The implantable cuff electrode according to claim 1, wherein the lips are movable upon modification of the distance of the edges with respect to each other in circumferential direction of the cuff relative to the cuff, while maintaining the sealing of the longitudinal slot.

5. The implantable cuff electrode according to claim 1, wherein the electrode array comprises at least two sensor surfaces separated from each other, which are arranged along a line in longitudinal direction of the cuff, wherein the at least two sensor surfaces are in electrical connection with each other via at least one conductor portion, wherein the at least one conductor portion can be deformed elastically during opening and closing of the cuff.

6. The implantable cuff electrode according to claim 5, wherein the at least one conductor portion is arranged in the inner wall and comprises meandering patterns arranged in the inner wall.

7. The implantable cuff electrode according to claim 6, wherein the line in cross section of the cuff electrode is located diametrically opposed to the longitudinal slot, and comprises the vertex of the bending line and cross section of the carrier.

8. The implantable cuff electrode according to claim 1, wherein the cuff is a silicone tube, in which the electrode array is arranged, wherein the electrode array is embedded in a carrier made from silicone material, and wherein the carrier comprises two longitudinal sides, which are guided out of the silicone tube and form the lips.

9. The implantable cuff electrode according to claim 1, wherein a cover layer is arranged above the longitudinal slot, which contributes to the fixation of the lips, and/or contributes to the sealing of the longitudinal slot.

* * * * *